United States Patent
Schmidt et al.

(10) Patent No.: US 10,351,493 B2
(45) Date of Patent: Jul. 16, 2019

(54) METHOD FOR PREPARING POLYUNSATURATED PERFLUORINATED COMPOUNDS

(71) Applicant: Arkema France, Colombes (FR)

(72) Inventors: Grégory Schmidt, Saint Andéol le Chateau (FR); Rémy Teissier, Francheville (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 16/090,857

(22) PCT Filed: Mar. 20, 2017

(86) PCT No.: PCT/FR2017/050636
§ 371 (c)(1),
(2) Date: Oct. 3, 2018

(87) PCT Pub. No.: WO2017/174890
PCT Pub. Date: Oct. 12, 2017

(65) Prior Publication Data
US 2019/0112243 A1 Apr. 18, 2019

(30) Foreign Application Priority Data
Apr. 4, 2016 (FR) ...................................... 16 52922

(51) Int. Cl.
C07C 17/20 (2006.01)
C07C 21/20 (2006.01)

(52) U.S. Cl.
CPC .......... *C07C 17/208* (2013.01); *C07C 17/206* (2013.01); *C07C 21/20* (2013.01)

(58) Field of Classification Search
CPC ........................... C07C 17/206; C07C 17/208
See application file for complete search history.

(56) References Cited

U.S. PATENT DOCUMENTS

| | | | |
|---|---|---|---|
| 2,844,636 A | 7/1958 | Neville et al. | |
| 3,287,425 A | 11/1966 | Maynard | |
| 6,198,011 B1* | 3/2001 | Chambers | C07B 39/00 570/170 |

FOREIGN PATENT DOCUMENTS

GB 798407 7/1958

OTHER PUBLICATIONS

Chambers et al., "Direct syntheses of pentakis(trifluoromethyl)cyclopentadienide salts and related systems", Canadian Journal of Chemistry, 1996, pp. 1925-1929, vol. 74, No. 11.
International Search Report (PCT/ISA/210) dated May 26, 2017, by the European Patent Office as the International Searching Authority for International Application No. PCT/FR2017/050636.
Written Opinion (PCT/ISA/237) dated May 26, 2017, by the European Patent Office as the International Searching Authority for International Application No. PCT/FR2017/050636.

* cited by examiner

*Primary Examiner* — Medhanit W Bahta
(74) *Attorney, Agent, or Firm* — Buchanan Ingersoll & Rooney P.C.

(57) ABSTRACT

The present invention relates to a method for preparing a polyinsaturated perfluorinated compound B from a polyinsaturated perhalogenated compound D having the formula $C_nX_{2(n-m+1)}$, in which X is independently selected from one of the halogens, F, Cl, Br or I, provided at least one X is not fluorine; n is the number of carbon atoms and is at least higher than or equal to 4, m is the number of double carbon-carbon bonds and is higher than or equal to 2, wherein the method comprises a step in which compound D is fluorinated in the presence of a fluorinating agent of general formula $AF_p$, in which A is hydrogen, an alkali metal or an alkaline earth metal, and p is 1 or 2, and in the presence of an aprotic organic polar solvent; the method being carried out with a molar ratio of $AF_p$ to compound D of less than $1.45*2(n-m+1)$.

10 Claims, No Drawings

METHOD FOR PREPARING POLYUNSATURATED PERFLUORINATED COMPOUNDS

TECHNICAL FIELD

The invention relates to a process for fluorinating perhalogenated compounds. In particular, the invention relates to the fluorination of polyunsaturated perhalogenated compounds in a liquid medium for forming compounds of perfluoro-polyunsaturated type.

TECHNOLOGICAL BACKGROUND OF THE INVENTION

Fluorinated compounds have a high potential in numerous fields of application. However, the use of many compounds is limited because of their method of preparation, which is sometimes expensive and/or difficult to implement.

For example, polyunsaturated perfluorinated compounds such as hexafluorobutadiene are used in the etching of electronic compounds. It is prepared by various processes involving $C_2$ coupling reactions and fluorination with fluorine $F_2$.

Another synthetic route consists in employing reactions for the fluorination of hexachlorobutadiene in the liquid phase. However, these reactions do not make possible the complete fluorination of hexachlorobutadiene to form hexafluorobutadiene. The fluorination of hexachlorobutadiene in the presence of potassium fluoride in order to form a mixture of 2,2-dichloroperfluoropropane and 2-chloro-2-hydroperfluoropropane is known in particular from U.S. Pat. No. 3,287,425.

The fluorination of perchlorohexatriene has also been demonstrated in the presence of $SbF_5$ at a temperature of 150° C. to 300° C. (U.S. Pat. No. 2,431,969). The final product comprises 12% of chlorine, which implies a solely partial fluorination of the perchlorohexatriene.

There thus still exists a need to make possible the preparation of fluorinated polyene compounds by selective and affordable reactions.

SUMMARY OF THE INVENTION

The present invention relates to a process for preparing a polyunsaturated perfluorinated compound B from a polyunsaturated perhalogenated compound D of formula $C_nX_{2(n-m+1)}$ wherein
X is chosen independently from a halogen F, Cl, Br or I, provided that at least one X is not a fluorine;
n is the number of carbon atoms and is at least greater than or equal to 4;
m is the number of carbon-carbon double bonds and is greater than or equal to 2; said process comprising the step of fluorinating the compound D in the presence of a fluorinating agent of general formula $AF_p$ wherein A is hydrogen, an alkali metal or an alkaline-earth metal, and p is 1 or 2; and in the presence of an aprotic polar organic solvent; said process being carried out with an $AF_p$/compound D molar ratio of less than 1.30*2(n−m+1).

According to one preferred embodiment, the compound D is a polyunsaturated perchlorinated compound of formula $C_nCl_{2(n-m+1)}$.

According to one preferred embodiment, the compound D is hexachlorobutadiene.

According to one preferred embodiment, the compound B is hexafluorobutadiene.

According to one preferred embodiment, the $AF_p$/compound D molar ratio is less than 1.15*2(n−m+1).

According to one preferred embodiment, the fluorinating agent is LiF, KF, NaF, $MgF_2$ or $CaF_2$.

According to one preferred embodiment, the aprotic polar organic solvent is chosen from the group consisting of an ether, an amide, an amine, a sulfoxide, a ketone, a nitrile and an ester.

According to one preferred embodiment, the aprotic polar organic solvent is chosen from the group consisting of 1,3-dioxane, 1,4-dioxane, 1,3,5-trioxane, tetrahydrofuran, 1,2-dimethoxyethane, dimethyl sulfoxide, diethyl sulfoxide, N-methylpyrrolidone, dimethylformamide, dimethylacetamide, ethyl acetate, acetone, propanone, 2-pentanone, butanone, n-butyl acetate, triethylamine, pyridine and acetonitrile.

According to one preferred embodiment, a first stream comprising the compound B, coproducts of the fluorination reaction and optionally of the unreacted compound D is recovered and separated by distillation so as to form a second stream comprising the coproducts of the reaction and the unreacted compound D and a third stream comprising the compound B, the coproducts preferably having the formula $C_nX_{2(n-m+1)}$ as defined in the present invention wherein at least one X is not a fluorine.

According to one particular embodiment, a compound of formula $AX_p$ is formed and the unreacted compound D is separated from the former and then recycled; A, X and p being as defined above.

DETAILED DESCRIPTION OF THE INVENTION

According to a first aspect, the present invention provides a process for preparing a polyunsaturated perfluorinated compound B. Advantageously, said polyunsaturated perfluorinated compound B can be obtained from a polyunsaturated perhalogenated compound D of formula $C_nX_{2(n-m+1)}$ wherein:
X is chosen independently from a halogen F, Cl, Br or I, provided that at least one X is not a fluorine;
n is the number of carbon atoms and is at least greater than or equal to 4;
m is the number of carbon-carbon double bonds and is greater than or equal to 2.

According to one preferred embodiment, said process comprises a step of fluorinating the compound D in the presence of a fluorinating agent.

Preferably, the fluorinating agent has the general formula $AF_p$ wherein A is hydrogen, an alkali metal or an alkaline-earth metal, and p is 1 or 2.

According to one preferred embodiment, the step of fluorinating the compound D is carried out in the presence of an aprotic polar organic solvent.

Thus, according to one preferred embodiment, the process according to the invention comprises a step of fluorinating the compound D in the presence of a fluorinating agent of general formula $AF_p$ wherein A is hydrogen, an alkali metal or an alkaline-earth metal, and p is 1 or 2; in the presence of an aprotic polar organic solvent.

Preferably, the step of fluorinating the compound D is carried out with an $AF_p$/compound D molar ratio of less than 1.45*2(n−m+1).

Thus, said process according to the present invention comprises a step of fluorinating the compound D in the presence of a fluorinating agent of general formula $AF_p$ wherein A is hydrogen, an alkali metal or an alkaline-earth metal, and p is 1 or 2; in the presence of an aprotic polar organic solvent; the $AF_p$/compound D molar ratio being less than 1.45*2(n−m+1)).

According to one preferred embodiment, the compound D is a compound of polyunsaturated perchlorinated type of formula $C_nCl_{2(n-m+1)}$. Preferably, the compound D is hexachlorobutadiene.

According to one embodiment, the compound B may be perfluorohexatriene or hexafluorobutadiene. Preferably, the compound B is hexafluorobutadiene.

According to one preferred embodiment, the $AF_p$/compound D molar ratio is less than 1.40*2(n−m+1); advantageously less than 1.30*2(n−m+1), preferably less than 1.25*2(n−m+1), more preferentially less than 1.15*2(n−m+1), in particular 1.10*2(n−m+1). This molar ratio close to the stoichiometry allows complete fluorination of the compound D contrary to what is known from the prior art.

Preferably, the fluorinating agent is LiF, KF, NaF, $MgF_2$ or $CaF_2$ or a mixture thereof. Preferably, the fluorinating agent is potassium fluoride KF.

According to one particular embodiment, the aprotic polar organic solvent is chosen from the group consisting of an ether, an amide, an amine, a sulfoxide, a ketone, a nitrile and an ester.

Advantageously, the aprotic polar organic solvent is chosen from the group consisting of 1,3-dioxane, 1,4-dioxane, 1,3,5-trioxane, tetrahydrofuran, 1,2-dimethoxyethane, dimethyl sulfoxide, diethyl sulfoxide, N-methylpyrrolidone, dimethylformamide, dimethylacetamide, ethyl acetate, acetone, propanone, 2-pentanone, butanone, n-butyl acetate, triethylamine, pyridine and acetonitrile.

Preferably, the aprotic polar organic solvent has a boiling point of greater than 100° C. at atmospheric pressure.

Thus, preferably, the aprotic polar organic solvent is 1,3-dioxane, 1,4-dioxane, 1,3,5-trioxane, N-methylpyrrolidone, dimethylformamide, dimethylacetamide, propanone, 2-pentanone, butanone, dimethyl sulfoxide or diethyl sulfoxide.

In particular, the aprotic polar organic solvent is chosen from the group consisting of 1,3-dioxane, 1,4-dioxane, 1,3,5-trioxane, dimethylformamide and dimethyl sulfoxide.

According to a preferred embodiment, the fluorinating step is carried out at the reflux of the solvent.

According to one preferred embodiment, the fluorinating step is carried out for a period of between 1 hour and 10 hours.

According to one preferred embodiment, a stream comprising the compound B is recovered and separated by distillation from the coproducts of the reaction and the unreacted compound D.

Preferably, the coproducts have the formula $C_nX_{2(n-m+1)}$ as defined by the present application, wherein at least one X is not a fluorine. The coproducts of the reaction can comprise monochloropentafluorinated compounds of formula $C_4F_5Cl$, and dichlorotetrafluorinated compounds of formula $C_4F_4Cl_2$.

According to one preferred embodiment, a compound of formula $AX_p$ is formed during the fluorinating step, A, X and p being as defined above. Advantageously, the unreacted compound D is separated from this compound $AX_p$ and then recycled so as to be used again in the fluorinating step of the present process. Said compound $AX_p$ may be KCl, LiCl, NaCl, $MgCl_2$ or $CaCl_2$.

EXAMPLE

The fluorinating step is carried out in a glass reactor fitted with a jacket, wherein a thermofluid regulated at the temperature T1 circulates, with a stirrer and with a thermometer and surmounted by a vertical condenser. The vertical condenser is cooled to a temperature T2 of −4° C. The condenser is connected to a stainless steel gas bottle cooled by dry ice. The following are introduced into the reactor:

500 ml of dimethylformamide;
87 g of hexachlorobutadiene (0.33 mol);
120 g of anhydrous potassium fluoride (6.2 mol) premilled and dried.

The reaction mixture is stirred and is brought to reflux over the course of 30 min, thus regulating the temperature T1 of the thermofluid circulating in the jacket of the reactor at 165° C. The starting product, the coproducts of the reaction and the solvent are at reflux, while only the $C_4F_6$ hexafluorobutadiene passes through the condenser. The latter is recovered by condensation in the dry ice trap. The reaction is stopped after 6 hours. 29 g of hexafluorobutadiene, measured by GC to be 99% pure, are recovered.

The invention claimed is:

1. A process for preparing a polyunsaturated perfluorinated compound B from a polyunsaturated perhalogenated compound D of formula $C_nX_{2(n-m+1)}$ wherein
X is chosen independently from a halogen F, Cl, Br or I, provided that at least one X is not a fluorine;
n is the number of carbon atoms and is at least greater than or equal to 4;
m is the number of carbon-carbon double bonds and is greater than or equal to 2;
said process comprising the step of fluorinating the compound D in the presence of a fluorinating agent of general formula $AF_p$ wherein A is hydrogen, an alkali metal or an alkaline-earth metal, and p is 1 or 2; and in the presence of an aprotic polar organic solvent; said process being carried out with an $AF_p$/compound D molar ratio of less than 1.30*2(n−m+1).

2. The process as claimed in claim 1, wherein the compound D is a polyunsaturated perchlorinated compound of formula $C_nCl_{2(n-m+1)}$.

3. The process as claimed in claim 1, wherein the compound D is hexachlorobutadiene.

4. The process as claimed in claim 1, wherein the compound B is hexafluorobutadiene.

5. The process as claimed in claim 1, wherein the $AF_p$/compound D molar ratio is less than 1.15*2(n−m+1).

6. The process as claimed in claim 1, wherein the fluorinating agent is LiF, KF, NaF, $MgF_2$ or $CaF_2$.

7. The process as claimed in claim 1, wherein the aprotic polar organic solvent is chosen from the group consisting of an ether, an amide, an amine, a sulfoxide, a ketone, a nitrile and an ester.

8. The process as claimed in claim 1, wherein the aprotic polar organic solvent is chosen from the group consisting of 1,3-dioxane, 1,4-dioxane, 1,3,5-trioxane, tetrahydrofuran, 1,2-dimethoxyethane, dimethyl sulfoxide, diethyl sulfoxide, N-methylpyrrolidone, dimethylformamide, dimethylacetamide, ethyl acetate, acetone, propanone, 2-pentanone, butanone, n-butyl acetate, triethylamine, pyridine and acetonitrile.

9. The process as claimed in claim 1, wherein a first stream comprising the compound B, coproducts of the fluorination reaction and optionally of the unreacted compound D is recovered and separated by distillation so as to form a second stream comprising the coproducts of the reaction and the unreacted compound D and a third stream comprising the compound B.

10. The process as claimed in claim 1, wherein a first stream comprising the compound B, coproducts of the fluorination reaction and unreacted compound D is recovered, and wherein a compound of formula $AX_p$ is formed and the unreacted compound D is separated from the compound of formula $AX_p$.

* * * * *